US008357517B2

(12) United States Patent
Weiss et al.

(10) Patent No.: US 8,357,517 B2
(45) Date of Patent: Jan. 22, 2013

(54) GENETIC ANALYSES PREDICTIVE OF ASTHMA

(75) Inventors: Scott Weiss, Chestnut Hill, MA (US); Marco Ramoni, Boston, MA (US); Blanca Himes, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 558 days.

(21) Appl. No.: 12/448,949

(22) PCT Filed: Jan. 16, 2008

(86) PCT No.: PCT/US2008/000524
§ 371 (c)(1),
(2), (4) Date: Jul. 16, 2009

(87) PCT Pub. No.: WO2008/088804
PCT Pub. Date: Jul. 24, 2008

(65) Prior Publication Data
US 2009/0325811 A1     Dec. 31, 2009

Related U.S. Application Data

(60) Provisional application No. 60/880,709, filed on Jan. 17, 2007.

(51) Int. Cl.
*C12P 19/34*      (2006.01)
(52) U.S. Cl. .................................................. 435/91.2
(58) Field of Classification Search ................ 435/91.2, 435/6.1
See application file for complete search history.

(56) References Cited

OTHER PUBLICATIONS

Thuong et al, PLoS Pathogens, vol. 4, Issue 12, pp. 1-13, Dec. 2008.*
Wacholder et al., Journal of national Cancer Institute, vol. 96, No. 6, pp. 434-442, 2004.*
International Search Report for PCT/US2008/000524 filed Jan. 16, 2008.
Written Opinion of the International Searching Authority for PCT/US2008/000524 filed Jan. 16, 2008.
International Preliminary Report on Patentability for PCT/US2008/000524 filed Jan. 16, 2008.
American Thoracic Society, "Standards for the Diagnosis and Care of Patients with Chronic Obstructive Pulmonary Disease (COPD) and Asthma," *Am. Rev. Respir. Dis.* 136(1):225-244 (1987).
Barber, et al., "The Quickhull Algorithm for Convex Hulls," *ACM Trans Math Softw* 22(4):469-483 (Dec. 1996).
Barnes, "Most difficult asthma originates primarily in adult life," *Paediatric Respir. Rev.* 7(2):141-144 (2006).
Baron, et al., "DNA Sequence Variants in Epithelium-Specific ETS-2 and ETS-3 Are Not Associated with Asthma," *Am. J. Respir. Crit. Care Med.* 166(7):927-932 (2002).
Camargo, et al., "Prospective Study of Body Mass Index, Weight Change, and Risk of Adult-onset Asthma in Women," *Arch. Intern. Med.* 159(21):2582-2588 (Nov. 1999).
Chae, et al., "Analysis of the polymorphisms in eotaxin gene family and their association with asthma, IgE, and eosinophil," *Biochem. Biophys. Res. Commun.* 320(1):131-137 (2004).
Christopherson, et al., "Chemokine Regulation of Normal and Pathologic Immune Responses," *Stem Cells* 19:388-396 (2001).
Colditz, "The Nurses' Health Study: A Cohort of US Women Followed Since 1976,"*JAMWA* 50(2):40-44 (Mar./Apr. 1995).
Cooper, et al., "A Bayesian Method for the Induction of Probablistic Networks from Data," *Machine Learning* 9(4):469-483 (1992).
Diebold, et al., "Innate Antiviral Responses by Means of TLR-7 Mediated Recognition of Single-Stranded RNA," *Science* 303(5663):1529-1531 (Mar. 2004).
Farrall, et al., "Gearing up for genome-wide gene-association studies," *Hum. Mol. Genet.* 14(Review Issue 2):R157-R162 (2005).
Friedman, et al., "Inferring Cellular Networks Using Probabilistic Graphical Models," *Science* 303(5659):799-805 (Feb. 2004).
Hakonarson, et al., "Allelic Frequencies and patterns of Single-nucleotide Polymorphisms in Candidate Genes for Asthma and Atopy in Iceland," *Am. J. Respir. Crit. Care Med.* 164(11):2036-2044 (2001).
Jansen, et al., "A Bayesian Networks Approach for Prediciting Protein-Protein Interactions from Genomic Data," *Science* 302(5644):449-453 (Oct. 2003).
Jenkins, et al., "Factors in childhood as predictors of asthma in adult life," *BMJ* 309(6947):90-93 (Jul. 1994).
Lamkhioued, et al., "Increased Expression of Eotaxin in Bronchoalveolar lavage and Airways of Asthmatics Contributes to the Chemotaxis of Eosinophils to the Site of Inflammation," *J. Immunol.* 159(9):4593-4601 (1997).
Lauritzen, et al., "Graphical Models for Genetic Analyses," *Statistical Science* 18(4):489-514 (2003).
Lazarus, et al., "Single nucleotide polymorphisms in innate immunity genes: abundant variation and potential role in complex human disease," *Immunol. Rev.* 190:9-25 (2002).
Lee, et al., "MCP-1, a highly expressed chemokine in dengue haemorrhagic fever/dengue shock syndrome patients, may cause permeability change, possibly through reduced tight junctions of vascular endothelium cells," *J. Gen. Virol.* 87(pt 12):3623-3630 (2006).
Lily, et al., "Elevated plasma eotaxin levels in patients with acute asthma," *J. Allergy Clin. Immunol.* 104(4 Pt 1):786-790 (Oct. 1999).
Means, et al., "The biology of Toll-like receptors," *Cytokine Growth Factor Rev.* 11(3):219-232 (2000).
Mir, et al., "Eosinophil-selective mediators in human strongyloidiasis," *Parasite Immunol.* 28:397-400 (2006).
Moisan, et al., "TLR7 ligand prevents allergen-induced airway hyperresponsiveness and eosinophilia in allergic asthma by a MYD88-dependent and MK2-independent pathway," *Am. J. Physiol. Lung Cell Mol. Physiol.* 290:L987-L995 (2006).

(Continued)

*Primary Examiner* — Gary Benzion
*Assistant Examiner* — Cynthia Wilder
(74) *Attorney, Agent, or Firm* — Law Office of: Michael A. Sanzo, LLC

(57) ABSTRACT

The present invention is directed to genetic sequence variations that can be used to predict whether a person will develop asthma. Disease is likely to occur if certain polymorphic forms the CCL11 gene, the CCL2 gene and the TLR7 gene are present.

16 Claims, 7 Drawing Sheets

OTHER PUBLICATIONS

Moorman, et al., "Increasing U.S. Asthma Mortality Rates: Who Is Really Dying?" *J. Asthma* 38(1):65-71 (2001).

Morris, et al., "Cooperative molecular and cellular networks regulate Toll-like receptor-dependent inflammatory responses," *FASEB J.* 20(12);2153-2155 (Oct. 2006).

Morris, et al., "Cooperative molecular and cellular networks regulate Toll-like receptor-dependent inflammatory responses," *FASEB J.* 20(12);E1539-E1549 (Oct. 2006).

Miyamasu, et al., "Variations in the human CC chemokine eotaxin gene," *Genes Immun.* 2(8):461-463 (2001).

Nakamura, et al., "Variant eotaxin: Its effects on the asthma phenotype," *J. Allergy Clin. Immunol.* 108(6):946-953 (2001).

Nicholson, et al., "Respiratory viruses and exacerbations of asthma in adults," BMJ 307(6910):982-986 (1993).

Ober, et al., "Asthma genetics 2006:the long and winding road to gene discovery," *Genes Immun.* 7(2):95-100 (2006).

Pisano, et al., "Diagnostic Performance of Digital versus Film Mammography for Breast-Cancer Screening," *N. Engl. J. Med.* 353(17):1773-1783 (Oct. 2005).

Punglia, et al., "Effect of Verification bias on Screening for Prostate Cancer by Measurement of Prostate-Specific Antigen," *N. Engl. J. Med.* 349(4):335-342 (Jul. 2003).

Raby, et al., "Eotaxin polymorphisms and serum total IgE levels in childre with asthma," *J. Allergy Clin. Immunol.* 117(2):298-305 (2006).

Rothenberg, et al., "Eotaxin. An Essential Mediator of Eosinophil Trafficking into Mucosal Tissues," *Am. J. Respir. Cell Mol. Biol.* 21(3):291-295 (1999).

Schatz, et al., "Sex Differences in the Presentation and Course of Asthma Hospitalizations," *Chest* 129(1):50-55 (Jan. 2006).

Sebastiani, et al., "Genetic dissection and prognostic modeling of overt stroke in sickle cell anemia," *Nat. Genet.* 37(4):435-440 (Apr. 2005).

Sebastiani, et al., "Minimal haplotype tagging," *Proc. Natl. Acad Sci. USA* 100(17):9900-9905 (Aug. 2003).

Shin, et al., "Association of Eotaxin gene family with asthma and serum total IgE," *Hum. Mol. Genet.* 12(11):1279-1285 (2003).

Sonna, et al., US Army Research Institute of environmental Medicine. Environmental Medicine Genome Bank Current Composition. USARIEM Techinical Note TN00-Jul. 8, 2000.

Stephens, et al., A New Statistical Method for Haplotype Reconstruction from Population Data, *Am. J. Hum. Genet.* 68(4):978-989 (2001).

Toelle, et al., "Childhood factors that predict asthma in young adulthood," *Eur. Respir. J.* 23(1):66-70 (2004).

Verzilli, et al., "Bayesian Graphical Models for Genomewide Association Studies," *Am. J. Hum. Genet.* 79(1):100-112 (Jul. 2006).

Ying, et al., "Enhanced expression of eotaxin and CCR3 mRNA and protein in atopic asthma. assocoation with airway hyperresponsiveness and predominant co-localization of eotaxin mRNA to bronchial epithelial and endothelial cells," *Eur. J. Immunol.* 27(12):3507-3516 (1997).

NCBI Database Accession No. BC033651.
NCBI Database Accession No. BC009716.
NCBI Database Accession No. NM013654.
NCBI Database Accession No. NM016562.
NCBI Database Accession No. NP057646.
NCBI Database Accession No. NM002986.
NCBI Database Accession No. NP002977.
NCBi Database Accession No. NM002982.
NCBI Database Accession No. NP002973.

* cited by examiner

```
   1 gaagactcca gatataggat cactccatgc catcaagaaa gttgatgcta ttgggcccat
  61 ctcaagctga tcttggcacc tctcatgctc tgctctcttc aaccagacct ctacattcca
 121 ttttggaaga agactaaaaa tggtgtttcc aatgtggaca ctgaagagac aaattcttat
 181 cctttttaac ataatcctaa tttccaaact ccttggggct agatggtttc ctaaaactct
 241 gccctgtgat gtcactctgg atgttccaaa gaaccatgtg atcgtggact gcacagacaa
 301 gcatttgaca gaaattcctg gaggtattcc cacgaacacc acgaacctca ccctcaccat
 361 taaccacata ccagacatct ccccagcgtc ctttcacaga ctggaccatc tggtagagat
 421 cgatttcaga tgcaactgtg tacctattcc actggggtca aaaaacaaca tgtgcatcaa
 481 gaggctgcag attaaaccca gaagctttag tggactcact tatttaaaat cccttacct
 541 ggatggaaac cagctactag agataccgca gggcctcccg cctagcttac agcttctcag
 601 ccttgaggcc aacaacatct tttccatcag aaaagagaat ctaacagaac tggccaacat
 661 agaaatactc tacctgggcc aaaactgtta ttatcgaaat ccttgttatg tttcatattc
 721 aatagagaaa gatgccttcc taaacttgac aaagttaaaa gtgctctccc tgaaagataa
 781 caatgtcaca gccgtcccta ctgttttgcc atctacttta acagaactat atctctacaa
 841 caacatgatt gcaaaaatcc aagaagatga ttttaataac ctcaaccaat tacaaattct
 901 tgacctaagt ggaaattgcc ctcgttgtta taatgcccca tttccttgtg cgccgtgtaa
 961 aaataattct ccctacaga tccctgtaaa tgcttttgat gcgctgacag aattaaaagt
1021 tttacgtcta cacagtaact ctcttcagca tgtgcccca agatggttta agaacatcaa
1081 caaactccag gaactggatc tgtcccaaaa cttcttggcc aaagaaattg gggatgctaa
1141 atttctgcat tttctcccca gcctcatcca attggatctg tctttcaatt ttgaacttca
1201 ggtctatcgt gcatctatga atctatcaca agcatttct tcactgaaaa gcctgaaaat
1261 tctgcggatc agaggatatg tctttaaaga gttgaaaagc tttaacctct cgccattaca
1321 taatcttcaa aatcttgaag ttcttgatct tggcactaac tttataaaaa ttgctaacct
1381 cagcatgttt aaacaattta aaagactgaa agtcatagat ctttcagtga ataaaatatc
1441 accttcagga gattcaagtg aagttggctt ctgctcaaat gccagaactt ctgtagaaag
1501 ttatgaaccc caggtcctgg aacaattaca ttatttcaga tatgataagt atgcaaggag
1561 ttgcagattc aaaaacaaag aggcttcttt catgtctgtt aatgaaagct gctacaagta
1621 tgggcagacc ttggatctaa gtaaaaatag tatatttttt gtcaagtcct ctgattttca
1681 gcatctttct ttcctcaaat gcctgaatct gtcaggaaat ctcattagcc aaactcttaa
1741 tggcagtgaa ttccaacctt tagcagagct gagatatttg gacttctcca caaccggct
1801 tgatttactc cattcaacag catttgaaga gcttcacaaa ctggaagttc tggatataag
1861 cagtaatagc cattattttc aatcagaagg aattactcat atgctaaact ttaccaagaa
1921 cctaaaggtt ctgcagaaac tgatgatgaa cgacaatgac atctcttcct ccaccagcag
1981 gaccatggag agtgagtctc ttagaactct ggaattcaga ggaaatcact tagatgtttt
2041 atggagagaa ggtgataaca gatacttaca attattcaag aatctgctaa aattagagga
2101 attagacatc tctaaaaatt ccctaagttt cttgccttct ggagttttg atggtatgcc
2161 tccaaatcta aagaatctct ctttggccaa aaatgggctc aaatctttca gttggaagaa
2221 actccagtgt ctaaagaacc tggaaacttt ggacctcagc acaaccaac tgaccactgt
2281 ccctgagaga ttatccaact gttccagaag cctcaagaat ctgattctta gaataatca
2341 aatcaggagt ctgacgaagt attttctaca agatgccttc cagttgcgat atctggatct
2401 cagctcaaat aaaatccaga tgatccaaaa gaccagcttc ccagaaaatg tcctcaacaa
2461 tctgaagatg ttgcttttgc atcataatcg gtttctgtgc acctgtgatg ctgtgtggtt
2521 tgtctggtgg gttaaccata cggaggtgac tattccttac ctggccacag atgtgacttg
2581 tgtggggcca ggagcacaca agggccaaag tgtgatctcc ctggatctgt acacctgtga
```

Figure 1

```
2641 gttagatctg actaacctga ttctgttctc actttccata tctgtatctc tctttctcat
2701 ggtgatgatg acagcaagtc acctctattt ctgggatgtg tggtatattt accatttctg
2761 taaggccaag ataaaggggt atcagcgtct aatatcacca gactgttgct atgatgcttt
2821 tattgtgtat gacactaaag acccagctgt gaccgagtgg gttttggctg agctggtggc
2881 caaactggaa gacccaagag agaaacattt taatttatgt ctcgaggaaa gggactggtt
2941 accagggcag ccagttctgg aaaacctttc ccagagcata cagcttagca aaaagacagt
3001 gtttgtgatg acagacaagt atgcaaagac tgaaaatttt aagatagcat tttacttgtc
3061 ccatcagagg ctcatggatg aaaaagttga tgtgattatc ttgatatttc ttgagaagcc
3121 ctttcagaag tccaagttcc tccagctccg gaaaaggctc tgtgggagtt ctgtccttga
3181 gtggccaaca aacccgcaag ctcacccata cttctggcag tgtctaaaga acgccctggc
3241 cacagacaat catgtggcct atagtcaggt gttcaaggaa acggtctagc ccttctttgc
3301 aaaacacaac tgcctagttt accaaggaga ggcctggctg tttaaattgt tttcatatat
3361 atcacaccaa aagcgtgttt tgaaattctt caagaaatga gattgcccat atttcagggg
3421 agccaccaac gtctgtcaca ggagttggaa agatggggtt tatataatgc atcaagtctt
3481 cttttcttatc tctctgtgtc tctatttgca cttgagtctc tcacctcagc tcctgtaaaa
3541 gagtggcaag taaaaaacat ggggctctga ttctcctgta attgtgataa ttaaatatac
3601 acacaatcat gacattgaga agaactgcat ttctacccttt aaaaagtact ggtatataca
3661 gaaatagggt taaaaaaaac tcaagctctc tctatatgag accaaaatgt actagagtta
3721 gtttagtgaa ataaaaaacc agtcagctgg ccgggcatgg tggctcatgc ttgtaatccc
3781 agcactttgg gaggccgagg caggtggatc acgaggtcag gagtttgaga ccagtctggc
3841 caacatggtg aaaccccgtc tgtactaaaa atacaaaaat tagctgggcg tggtggtggg
3901 tgcctgtaat cccagctact gggaggctg aggcaggaga atcgcttgaa cccgggaggt
3961 ggaggtggca gtgagccgag atcacgccac tgcaatgcag cccgggcaac agagctagac
4021 tgtctcaaaa gaacaaaaaa aaaaaaacac aaaaaaactc agtcagcttc ttaaccaatt
4081 gcttccgtgt catccagggc cccattctgt gcagattgag tgtgggcacc acacaggtgg
4141 ttgctgcttc agtgcttcct gctctttttc cttgggcctg cttctgggtt ccatagggaa
4201 acagtaagaa agaaagacac atccttacca taaatgcata tggtccacct acaaatagaa
4261 aaatatttaa atgatctgcc tttatacaaa gtgatattct ctacctttga taatttaccet
4321 gcttaaatgt ttttatctgc actgcaaagt actgtatcca aagtaaaatt tcctcatcca
4381 atatctttca aactgttttg ttaactaatg ccatatattt gtaagtatct gcacacttga
4441 tacagcaacg ttagatggtt ttgatggtaa accctaaagg aggactccaa gagtgtgtat
4501 ttatttatag ttttatcaga gatgacaatt atttgaatgc caattatatg gattcctttc
4561 attttttgct ggaggatggg agaagaaacc aaagtttata gaccttcaca ttgagaaagc
4621 ttcagttttg aacttcagct atcagattca aaaacaacag aaagaaccaa gacattctta
4681 agatgcctgt actttcagct gggtataaat tcatgagttc aaagattgaa acctgaccaa
4741 tttgctttat ttcatggaag aagtgatcta caaaggtgtt tgtgccattt ggaaaacagc
4801 gtgcatgtgt tcaagcctta gattggcgat gtcgtatttt cctcacgtgt ggcaatgcca
4861 aaggctttac tttacctgtg agtacacact atatgaatta tttccaacgt acatttaatc
4921 aataagggtc acaaattccc aaatcaatct ctggaataaa tagagaggta attaaattgc
4981 tggagccaac ta
```

Figure 1 (continued)

```
   1 mvfpmwtlkr qililfniil iskllgarwf pktlpcdvtl dvpknhvivd ctdkhlteip
  61 ggiptnttnl tltinhipdi spasfhrldh lveidfrcnc vpiplgsknn mcikrlqikp
 121 rsfsgltylk slyldgnqll eipqglppsl qllsleanni fsirkenlte lanieilylg
 181 qncyyrnpcy vsysiekdaf lnltklkvls lkdnnvtavp tvlpstltel ylynnmiaki
 241 qeddfnnlnq lqildlsgnc prcynapfpc apcknnsplq ipvnafdalt elkvlrlhsn
 301 slqhvpprwf kninklqeld lsqnflakei gdakflhflp sliqldlsfn felqvyrasm
 361 nlsqafsslk slkilrirgy vfkelksfnl splhnlqnle vldlgtnfik ianlsmfkqf
 421 krlkvidlsv nkispsgdss evgfcsnart svesyepqvl eqlhyfrydk yarscrfknk
 481 easfmsvnes cykygqtldl sknsiffvks sdfqhlsflk clnlsgnlis qtlngsefqp
 541 laelryldfs nnrldllhst afeelhklev ldissnshyf qsegithmln ftknlkvlqk
 601 lmmndndiss stsrtmeses lrtlefrgnh ldvlwregdn rylqlfknll kleeldiskn
 661 slsflpsgvf dgmppnlknl slaknglksf swkklqclkn letldlshnq lttvperlsn
 721 csrslknlil knnqirsltk yflqdafqlr yldlssnkiq miqktsfpen vlnnlkmlll
 781 hhnrflctcd avwfvwwvnh tevtipylat dvtcvgpgah kgqsvisldl ytceldltnl
 841 ilfslsisvs lflmvmmtas hlyfwdvwyi yhfckakikg yqrlispdcc ydafivydtk
 901 dpavtewvla elvakledpr ekhfnlclee rdwlpgqpvl enlsqsiqls kktvfvmtdk
 961 yaktenfkia fylshqrlmd ekvdviilif lekpfqkskf lqlrkrlcgs svlewptnpq
1021 ahpyfwqclk nalatdnhva ysqvfketv
```

Figure 2

```
   1 atgggcaaag gcttccctgg aatctcccac actgtctgct ccctataaaa ggcaggcaga
  61 tgggccagag gagcagagag gctgagacca acccagaaac caccacctct cacgccaaag
 121 ctcacacctt cagcctccaa catgaaggtc tccgcagcac ttctgtggct gctgctcata
 181 gcagctgcct tcagccccca ggggctcgct gggccagctt ctgtcccaac cacctgctgc
 241 tttaacctgg ccaataggaa gatacccctt cagcgactag agagctacag gagaatcacc
 301 agtggcaaat gtccccagaa agctgtgatc ttcaagacca aactggccaa ggatatctgt
 361 gccgacccca agaagaagtg ggtgcaggat tccatgaagt atctggacca aaaatctcca
 421 actccaaagc cataaataat caccattttt gaaaccaaac cagagcctga gtgttgccta
 481 atttgttttc ccttcttaca atgcattctg aggtaacctc attatcagtc caagggcat
 541 gggttttatt atatatatat attttttttt ttaaaaaaaa aacgtattgc atttaattta
 601 ttgaggcttt aaaacttatc ctccatgaat atcagttatt tttaaactgt aaagctttgt
 661 gcagattctt taccccctgg gagccccaat tcgatcccct gtcacgtgtg gcaatgttc
 721 cccctctcct ctcttcctcc ctggaatctt gtaaaggtcc tgcaaagat gatcagtatg
 781 aaaatgtcat tgttcttgtg aacccaaagt gtgactcatt aaatggaagt aaatgttgtt
 841 ttaggaatac ataaagtatg tgcatatttt attatagtca ctagttgtaa tttttttgtg
 901 ggaaatccac actgagctga ggggg
```

Figure 3

```
  1 mkvsaallwl lliaaafspq glagpasvpt tccfnlanrk iplqrlesyr ritsgkcpqk
 61 avifktklak dicadpkkkw vqdsmkyldq ksptpkp
```

Figure 4

```
  1 gaggaaccga gaggctgaga ctaacccaga aacatccaat tctcaaactg aagctcgcac
 61 tctcgcctcc agcatgaaag tctctgccgc ccttctgtgc ctgctgctca tagcagccac
121 cttcattccc caagggctcg ctcagccaga tgcaatcaat gccccagtca cctgctgtta
181 taacttcacc aataggaaga tctcagtgca gaggctcgcg agctatagaa gaatcaccag
241 cagcaagtgt cccaaagaag ctgtgatctt caagaccatt gtggccaagg agatctgtgc
301 tgaccccaag cagaagtggg ttcaggattc catggaccac tggacaagc aaacccaaac
361 tccgaagact tgaacactca ctccacaacc caagaatctg cagctaactt attttcccct
421 agctttcccc agacaccctg ttttatttta ttataatgaa ttttgtttgt tgatgtgaaa
481 cattatgcct taagtaatgt taattcttat ttaagttatt gatgttttaa gtttatcttt
541 catggtacta gtgtttttta gatacagaga cttggggaaa ttgcttttcc tcttgaacca
601 cagttctacc cctgggatgt tttgagggtc tttgcaagaa tcattaatac aaagaatttt
661 ttttaacatt ccaatgcatt gctaaaatat tattgtggaa atgaatattt tgtaactatt
721 acaccaaata aatatatttt tgtacaaaaa aaaaaaaaa
```

Figure 5

```
  1 mkvsaallcl lliaatfipq glaqpdaina pvtccynftn rkisvqrlas yrritsskcp
 61 keavifktiv akeicadpkq kwvqdsmdhl dkqtqtpkt
```

Figure 6

| Gene | refseq position | rs number | Chromosome location | FLANKING SEQUENCES | SEQ ID NO: |
|---|---|---|---|---|---|
| TLR7 | 007154 | rs179019 | chrX: 12799890 | 5':CCCAGGGGGTGCCCAGGGGCCTTTCTGACTGTTGGTTAGTTGGGTAAA AGAGTAGAGTCAGGAGAGCAGGAGAAATCCTTTCTTAACTCACTATAAAAATA [C/A] 3':AAGCGTTCCCCAGGCCTCAAATAGTCTCATCTCAAGATAAATTTCCTTT TGCCAAGANTGCTGCTGAAAAATAATCCATTGTAGCCAGATAATAGCTATGC | SEQ ID NO:7 |
| | 007042 | rs179020 | chrX: 12799778 | 5':TCCTTTNAAACTCAGGCAACTTGGCTTTTTCTGCTCTGTGATCTTGAA AGTNGCTTGGAGGAACAGCTGAGTGCATGGGCGTGTTGTCCTCTCAGGGCT [G/A] 3':ACATGTTGTAGCCCAGGGGTGCCCAGGGCCTTTCTGACTGGTTGGTT AGTTGGGTAAAAGAGTAGAGTCAGGAGAGCAGGAGAAATCCTTTCTTAACTCA | SEQ ID NO:8 |
| | 010982 | rs179017 | chrX: 12803714 | 5':GACCCAGNGGAGGTAANTGAATCATGGGGCGGGTTTTCCCATGCTG TTCTCATGATAGTGGATAAGTCTCACAAGATCTGATGGTTTCATAAACGGC [A/C] 3':GTTCCCCTGCACATGCTCTCTTGCCTGACGCCATGTAAGACNTAATTTT GCTCCTCCTTCACCTTCCACCATGATTGTGAGGCCTCCTCAGTCATGTGGA | SEQ ID NO:9 |

Figure 7

| Gene | refseq position | rs number | Chromosome location | FLANKING SEQUENCES | SEQ ID NO: |
|---|---|---|---|---|---|
| | 005208 | rs1129844 | chr17: 29637007 | 5': TCTCACGCCAAAGTCACACCTTCAGCCTCAGCCTCCAACATGAAGGTCTCCGCA GCACTTCGTGGCTGCTGCTCATAGCAGCTGCCTTCAGCCCTCAGCCCCCAGGGGCTC [G/A] 3': CTGGGCCAGTAAGCCCCCCAACTCCTTACAGGAAAGGTAAGGTAACCA CCTCCAGAGCTACTAGGTCAGCAAGAATCTTTACAGACNCACTGCAAATTC | SEQID NO:10 |
| CCL11 | 004654 | rs 17735961 | chr17: 29636453 | 5': GGTGTGTTGTGTCCTTCCTGGTTCAGAGATGCAACTATGTGCAGGGCTGCT GAGCTCCTCTGCATCTGGGTGGGAGCCTAATGAAGTTTTGGGGCTCCTT [C/A] 3': CTGGTCTCCAAAATCCTCAAGACCACCATGTGAACACAGGAATCAAGGA AGGTTCTTAGATCGACTCATCCCCCAGGCCTTTGGTTTCCTTGCTCCTTTC | SEQ ID NO:11 |
| | 003760 | rs4795895 | chr17: 29635559 | 5': GGTTAAGTAAGTTGTCCATGGTATCACAGCTAGTCAGTCACAGAGCCAT CATCCAAATGCAGATATCCTGAATTCAGGTTCTACATTAGACTAACCACC [G/A] 3' GGAATGGAGCAGGAAAGAACAGGAAGACTCCACATTTTGGCCTCTAT TTGGTAATTATAGTTAACTTTTTAGGTAATTATAGACCAATTATCCTAGAT | SEQ ID NO:12 |

Figure 7 (continued)

| Gene | refseq position | rs number | Chromosome location | FLANKING SEQUENCES | SEQ ID NO: |
|---|---|---|---|---|---|
| CCL2 | 005972 | rs4586 | chr17: 29607382 | 5': TCTTTTCTGCTCTTAAGATCAGAATAATCCAGTTCATCCTAAAATGCTT TTTCTTTGTGGTTTATTTTCCAGATGCAATCAATGCCCAGTCACCTGCTG [T/C] 3': TATAACTTCACCAATAGGAAGATCTCAGTGCAGAGGCTCGCGAGCTATA GAAGAATCACCAGCAGCAAGTGTCCCAAAGAAGCTGTGATGTGAGTTCAGC | SEQ ID NO:13 |

Figure 7 (continued)

SEQUENCE LISTING

<160> NUMBER OF SEQ ID NOS: 13

<210> SEQ ID NO 1
<211> LENGTH: 4992
<212> TYPE: DNA
<213> ORGANISM: Homo sapiens

<400> SEQUENCE: 1

| | | | | | | |
|---|---|---|---|---|---|---|
| gaagactcca | gatataggat | cactccatgc | catcaagaaa | gttgatgcta | ttgggcccat | 60 |
| ctcaagctga | tcttggcacc | tctcatgctc | tgctctcttc | aaccagacct | ctacattcca | 120 |
| tttttggaaga | agactaaaaa | tggtgtttcc | aatgtggaca | ctgaagagac | aaattcttat | 180 |
| ccttttaac | ataatcctaa | tttccaaact | ccttggggct | agatggtttc | ctaaaactct | 240 |
| gccctgtgat | gtcactctgg | atgttccaaa | gaaccatgtg | atcgtggact | gcacagacaa | 300 |
| gcatttgaca | gaaattcctg | gaggtattcc | cacgaacacc | acgaacctca | ccctcaccat | 360 |
| taaccacata | ccagacatct | ccccagcgtc | ctttcacaga | ctggaccatc | tggtagagat | 420 |
| cgatttcaga | tgcaactgtg | tacctattcc | actggggtca | aaaaacaaca | tgtgcatcaa | 480 |
| gaggctgcag | attaaaccca | gaagctttag | tggactcact | tatttaaaat | ccctttacct | 540 |
| ggatggaaac | cagctactag | ataccgca | gggcctcccg | cctagcttac | agcttctcag | 600 |
| ccttgaggcc | aacaacatct | tttccatcag | aaaagagaat | ctaacagaac | tggccaacat | 660 |
| agaaatactc | tacctgggcc | aaaactgtta | ttatcgaaat | ccttgttatg | tttcatattc | 720 |
| aatagagaaa | gatgccttcc | taaacttgac | aaagttaaaa | gtgctctccc | tgaaagataa | 780 |
| caatgtcaca | gccgtcccta | ctgttttgcc | atctactta | acagaactat | atctctacaa | 840 |
| caacatgatt | gcaaaaatcc | aagaagatga | ttttaataac | ctcaaccaat | acaaattct | 900 |
| tgacctaagt | ggaaattgcc | ctcgttgtta | taatgcccca | tttccttgtg | cgccgtgtaa | 960 |
| aaataattct | cccctacaga | tccctgtaaa | tgcttttgat | gcgctgacag | aattaaaagt | 1020 |
| tttacgtcta | cacagtaact | ctcttcagca | tgtgccccca | agatggttta | agaacatcaa | 1080 |
| caaactccag | gaactggatc | tgtcccaaaa | cttcttggcc | aaagaaattg | gggatgctaa | 1140 |
| atttctgcat | tttctcccca | gcctcatcca | attggatctg | tctttcaatt | ttgaacttca | 1200 |
| ggtctatcgt | gcatctatga | atctatcaca | agcattttct | tcactgaaaa | gcctgaaaat | 1260 |
| tctgcggatc | agaggatatg | tctttaaaga | gttgaaaagc | tttaacctct | cgccattaca | 1320 |
| taatcttcaa | aatcttgaag | ttcttgatct | tggcactaac | tttataaaaa | ttgctaacct | 1380 |
| cagcatgttt | aaacaattta | aaagactgaa | agtcatagat | ctttcagtga | ataaaatatc | 1440 |
| accttcagga | gattcaagtg | aagttggctt | ctgctcaaat | gccagaactt | ctgtagaaag | 1500 |
| ttatgaaccc | caggtcctgg | aacaattaca | ttatttcaga | tatgataagt | atgcaaggag | 1560 |
| ttgcagattc | aaaacaaag | aggcttcttt | catgtctgtt | aatgaaagct | gctacaagta | 1620 |
| tgggcagacc | ttggatctaa | gtaaaaatag | tatatttttt | gtcaagtcct | ctgattttca | 1680 |
| gcatctttct | ttcctcaaat | gcctgaatct | gtcaggaaat | ctcattagcc | aaactcttaa | 1740 |
| tggcagtgaa | ttccaacctt | tagcagagct | gagatatttg | gacttctcca | caaccggct | 1800 |
| tgatttactc | cattcaacag | catttgaaga | gcttcacaaa | ctggaagttc | tggatataag | 1860 |
| cagtaatagc | cattattttc | aatcagaagg | aattactcat | atgctaaact | ttaccaagaa | 1920 |
| cctaaaggtt | ctgcagaaac | tgatgatgaa | cgacaatgac | atctcttcct | ccaccagcag | 1980 |
| gaccatggag | agtgagtctc | ttagaactct | ggaattcaga | ggaaatcact | tagatgtttt | 2040 |

```
atggagagaa ggtgataaca gatacttaca attattcaag aatctgctaa aattagagga    2100
attagacatc tctaaaaatt ccctaagttt cttgccttct ggagttttg atggtatgcc     2160 tccaaatcta aagaatctct ctttggccaa aaatgggctc aaatctttca gttggaagaa    2220
actccagtgt ctaaagaacc tggaaacttt ggacctcagc cacaaccaac tgaccactgt    2280
ccctgagaga ttatccaact gttccagaag cctcaagaat ctgattctta agaataatca    2340
aatcaggagt ctgacgaagt attttctaca agatgccttc cagttgcgat atctggatct    2400
cagctcaaat aaaatccaga tgatccaaaa gaccagcttc cagaaaatg tcctcaacaa     2460 tctgaagatg ttgcttttgc atcataatcg gtttctgtgc acctgtgatg ctgtgtggtt    2520
tgtctggtgg gttaaccata cggaggtgac tattccttac ctggccacag atgtgacttg    2580 tgtgggggcca ggagcacaca agggccaaag tgtgatctcc ctggatctgt acacctgtga   2640
gttagatctg actaacctga ttctgttctc actttccata tctgtatctc tctttctcat    2700
ggtgatgatg acagcaagtc acctctattt ctgggatgtg tggtatattt accatttctg    2760
taaggccaag ataaaggggt atcagcgtct aatatcacca gactgttgct atgatgcttt    2820
tattgtgtat gacactaaag acccagctgt gaccgagtgg gttttggctg agctggtggc    2880
caaactggaa gacccaagag agaaacattt taatttatgt ctcgaggaaa gggactggtt    2940
accagggcag ccagttctgg aaaaccttc ccagagcata cagcttagca aaaagacagt     3000
gtttgtgatg acagacaagt atgcaaagac tgaaaatttt aagatagcat tttacttgtc    3060
ccatcagagg ctcatggatg aaaaagttga tgtgattatc ttgatatttc ttgagaagcc    3120 cttttcagaag tccaagttcc tccagctccg gaaaaggctc tgtgggagtt ctgtccttga   3180
gtggccaaca aacccgcaag ctcacccata cttctggcag tgtctaaaga acgccctggc    3240
cacagacaat catgtggcct atagtcaggt gttcaaggaa acggtctagc ccttctttgc    3300
aaaacacaac tgcctagttt accaaggaga ggcctggctg tttaaattgt tttcatatat    3360
atcacaccaa aagcgtgttt tgaaattctt caagaaatga gattgcccat atttcagggg    3420
agccaccaac gtctgtcaca ggagttggaa agatggggtt tatataatgc atcaagtctt    3480 cttttcttatc tctctgtgtc tctatttgca cttgagtctc tcacctcagc tcctgtaaaa    3540
gagtggcaag taaaaaacat ggggctctga ttctcctgta attgtgataa ttaaatatac    3600
acacaatcat gacattgaga agaactgcat ttctaccctt aaaaagtact ggtatataca    3660
gaaatagggt taaaaaaaac tcaagctctc tctatatgag accaaaatgt actagagtta    3720
gtttagtgaa ataaaaaacc agtcagctgg ccgggcatgg tggctcatgc ttgtaatccc    3780
agcactttgg gaggccgagg caggtggatc acgaggtcag gagtttgaga ccagtctggc    3840
caacatggtg aaacccgtc tgtactaaaa atacaaaaat tagctgggcg tggtggtggg    3900
tgcctgtaat cccagctact gggaggctg aggcaggaga atcgcttgaa cccgggaggt     3960
ggaggtggca gtgagccgag atcacgccac tgcaatgcag cccgggcaac agagctagac    4020
tgtctcaaaa gaacaaaaaa aaaaaaacac aaaaaaactc agtcagcttc ttaaccaatt    4080
gcttccgtgt catccagggc cccattctgt gcagattgag tgtgggcacc acacaggtgg    4140
ttgctgcttc agtgcttcct gctcttttc cttgggcctg cttctggggt ccatagggaa     4200
acagtaagaa agaaagacac atccttacca taaatgcata tggtccacct acaaatagaa    4260
aaatatttaa atgatctgcc tttatacaaa gtgatattct ctacctttga taatttacct    4320
gcttaaatgt ttttatctgc actgcaaagt actgtatcca aagtaaaatt tcctcatcca    4380
atatctttca aactgttttg ttaactaatg ccatatattt gtaagtatct gcacacttga    4440
```

-continued

```
tacagcaacg ttagatggtt ttgatggtaa accctaaagg aggactccaa gagtgtgtat    4500
ttatttatag ttttatcaga gatgacaatt atttgaatgc caattatatg gattcctttc    4560
attttttgct ggaggatggg agaagaaacc aaagtttata gaccttcaca ttgagaaagc    4620
ttcagttttg aacttcagct atcagattca aaaacaacag aaagaaccaa gacattctta    4680
agatgcctgt actttcagct gggtataaat tcatgagttc aaagattgaa acctgaccaa    4740
tttgctttat ttcatggaag aagtgatcta caaaggtgtt tgtgccattt ggaaaacagc    4800
gtgcatgtgt tcaagcctta gattggcgat gtcgtatttt cctcacgtgt ggcaatgcca    4860
aaggctttac tttacctgtg agtacacact atatgaatta tttccaacgt acatttaatc    4920
aataagggtc acaaattccc aaatcaatct ctggaataaa tagagaggta attaaattgc    4980
tggagccaac ta                                                       4992
```

<210> SEQ ID NO 2
<211> LENGTH: 1049
<212> TYPE: PRT
<213> ORGANISM: Homo sapiens

<400> SEQUENCE: 2

```
Met Val Phe Pro Met Trp Thr Leu Lys Arg Gln Ile Leu Ile Leu Phe
1               5                  10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270
```

```
Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
        290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
                340                 345                 350

Leu Gln Val Tyr Arg Ala Ser Met Asn Leu Ser Gln Ala Phe Ser Ser
            355                 360                 365

Leu Lys Ser Leu Lys Ile Leu Arg Ile Arg Gly Tyr Val Phe Lys Glu
        370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
                420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
        450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
        530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
        610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
                660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
        690                 695                 700
```

-continued

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
            725                 730                 735

Ser Leu Thr Lys Tyr Phe Leu Gln Asp Ala Phe Gln Leu Arg Tyr Leu
        740                 745                 750

Asp Leu Ser Ser Asn Lys Ile Gln Met Ile Gln Lys Thr Ser Phe Pro
    755                 760                 765

Glu Asn Val Leu Asn Asn Leu Lys Met Leu Leu Leu His His Asn Arg
770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
            805                 810                 815

Pro Gly Ala His Lys Gly Gln Ser Val Ile Ser Leu Asp Leu Tyr Thr
        820                 825                 830

Cys Glu Leu Asp Leu Thr Asn Leu Ile Leu Phe Ser Leu Ser Ile Ser
    835                 840                 845

Val Ser Leu Phe Leu Met Val Met Met Thr Ala Ser His Leu Tyr Phe
850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
            885                 890                 895

Tyr Asp Thr Lys Asp Pro Ala Val Thr Glu Trp Val Leu Ala Glu Leu
        900                 905                 910

Val Ala Lys Leu Glu Asp Pro Arg Glu Lys His Phe Asn Leu Cys Leu
    915                 920                 925

Glu Glu Arg Asp Trp Leu Pro Gly Gln Pro Val Leu Glu Asn Leu Ser
930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
            965                 970                 975

Arg Leu Met Asp Glu Lys Val Asp Val Ile Ile Leu Ile Phe Leu Glu
        980                 985                 990

Lys Pro Phe Gln Lys Ser Lys Phe Leu Gln Leu Arg Lys Arg Leu Cys
    995                 1000                1005

Gly Ser Ser Val Leu Glu Trp Pro Thr Asn Pro Gln Ala His Pro
    1010                1015                1020

Tyr Phe Trp Gln Cys Leu Lys Asn Ala Leu Ala Thr Asp Asn His
    1025                1030                1035

Val Ala Tyr Ser Gln Val Phe Lys Glu Thr Val
    1040                1045

<210> SEQ ID NO 3
<211> LENGTH: 925
<212> TYPE: DNA
<213> ORGANISM: Homo sapiens

<400> SEQUENCE: 3
atgggcaaag gcttccctgg aatctcccac actgtctgct ccctataaaa ggcaggcaga     60
tgggccagag gagcagagag gctgagacca acccagaaac caccacctct cacgccaaag    120
ctcacacctt cagcctccaa catgaaggtc tccgcagcac ttctgtggct gctgctcata    180

-continued

```
gcagctgcct tcagccccca ggggctcgct gggccagctt ctgtcccaac cacctgctgc      240
tttaacctgg ccaataggaa gatacccctt cagcgactag agagctacag gagaatcacc      300
agtggcaaat gtccccagaa agctgtgatc ttcaagacca aactggccaa ggatatctgt      360
gccgacccca agaagaagtg ggtgcaggat tccatgaagt atctggacca aaaatctcca      420
actccaaagc cataaataat caccattttt gaaaccaaac cagagcctga gtgttgccta      480
atttgttttc ccttcttaca atgcattctg aggtaacctc attatcagtc caagggcat       540 gggttttatt atatatatat attttttttt ttaaaaaaaa aacgtattgc atttaattta      600
ttgaggcttt aaaacttatc ctccatgaat atcagttatt tttaaactgt aaagctttgt      660
gcagattctt tacccccctgg gagccccaat tcgatcccct gtcacgtgtg ggcaatgttc     720 ccctctcct ctcttcctcc ctggaatctt gtaaaggtcc tggcaaagat gatcagtatg       780
aaaatgtcat tgttcttgtg aacccaaagt gtgactcatt aaatggaagt aaatgttgtt      840
ttaggaatac ataaagtatg tgcatatttt attatagtca ctagttgtaa ttttttttgtg     900 ggaaatccac actgagctga ggggg                                            925
```

<210> SEQ ID NO 4
<211> LENGTH: 97
<212> TYPE: PRT
<213> ORGANISM: Homo sapiens

<400> SEQUENCE: 4

```
Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
            20                  25                  30

Cys Phe Asn Leu Ala Asn Arg Lys Ile Pro Leu Gln Arg Leu Glu Ser
        35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro
```

<210> SEQ ID NO 5
<211> LENGTH: 760
<212> TYPE: DNA
<213> ORGANISM: Homo sapiens

<400> SEQUENCE: 5

```
gaggaaccga gaggctgaga ctaacccaga aacatccaat tctcaaactg aagctcgcac       60
tctcgcctcc agcatgaaag tctctgccgc ccttctgtgc ctgctgctca tagcagccac      120
cttcattccc caagggctcg ctcagccaga tgcaatcaat gccccagtca cctgctgtta     180
taacttcacc aataggaaga tctcagtgca gaggctcgcg agctatagaa gaatcaccag      240
cagcaagtgt cccaaagaag ctgtgatctt caagaccatt gtggccaagg agatctgtgc      300
tgaccccaag cagaagtggg ttcaggattc catggaccac ctggacaagc aaacccaaac      360
tccgaagact tgaacactca ctccacaacc caagaatctg cagctaactt attttcccct      420
agctttcccc agacaccctg ttttatttta ttataatgaa ttttgtttgt tgatgtgaaa      480
cattatgcct taagtaatgt taattcttat ttaagttatt gatgttttaa gtttatcttt      540
```

```
catggtacta gtgttttta gatacagaga cttggggaaa ttgcttttcc tcttgaacca        600
cagttctacc cctgggatgt tttgagggtc tttgcaagaa tcattaatac aaagaatttt        660
ttttaacatt ccaatgcatt gctaaaatat tattgtggaa atgaatattt tgtaactatt        720
acaccaaata aatatatttt tgtacaaaaa aaaaaaaaaa                              760
```

```
<210> SEQ ID NO 6
<211> LENGTH: 99
<212> TYPE: PRT
<213> ORGANISM: Homo sapiens

<400> SEQUENCE: 6

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 7
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is C or A
<220> FEATURE:
<221> NAME/KEY: misc_feature
<222> LOCATION: (159)..(159)
<223> OTHER INFORMATION: n is A, G, C or T

<400> SEQUENCE: 7 cccaggggt gcccagggc ctttctgact ggttggttag ttgggtaaaa gagtagagtc        60
aggagagcag gaaatccttt cttaactcac tataaaata naagcgttcc ccaggcctca        120
aatagtctca tctcaagata aatttccttt tgccaagant gctgctgaaa ataatccatt        180
gtagccagat aatagctatg c                                                  201

<210> SEQ ID NO 8
<211> LENGTH: 201
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is A, G, C or T
<220> FEATURE:
<221> NAME/KEY: misc_feature
<222> LOCATION: (53)..(53)
<223> OTHER INFORMATION: n is A, G, C or T
<220> FEATURE:
<221> NAME/KEY: misc_feature
<222> LOCATION: (101)..(101)
<223> OTHER INFORMATION: n is G or A
```

-continued

<400> SEQUENCE: 8
tcctttnaaa ctcaggcaac ttggctttt tctgctctgt gatcttgaaa gtngcttgga 60
ggaacagctg agtgcatggg gctgttgtcc tctcagggct nacatgttgt agcccagggg 120
gtgcccaggg gcctttctga ctggttggtt agttgggtaa aagagtagag tcaggagagc 180
aggaaatcct ttcttaactc a 201

<210> SEQ ID NO 9
<211> LENGTH: 201
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is A, G, C or T
<220> FEATURE:
<221> NAME/KEY: misc_feature
<222> LOCATION: (18)..(18)
<223> OTHER INFORMATION: n is A, G, C or T
<220> FEATURE:
<221> NAME/KEY: misc_feature
<222> LOCATION: (101)..(101)
<223> OTHER INFORMATION: n is A or C
<220> FEATURE:
<221> NAME/KEY: misc_feature
<222> LOCATION: (143)..(143)
<223> OTHER INFORMATION: n is A, G, C or T

<400> SEQUENCE: 9
gacccagngg gaggtaantg aatcatgggg gcgggttttt cccatgctgt tctcatgata 60
gtggataagt ctcacaagat ctgatggttt cataaacggc ngttcccctg cacatgctct 120
cttgcctgac gccatgtaag acntaatttt gctcctcctt caccttccac catgattgtg 180
aggcctcctc agtcatgtgg a 201

<210> SEQ ID NO 10
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is G or A
<220> FEATURE:
<221> NAME/KEY: misc_feature
<222> LOCATION: (189)..(189)
<223> OTHER INFORMATION: n is A, G, C or T

<400> SEQUENCE: 10
tctcacgcca agctcacac cttcagcctc caacatgaag gtctccgcag cacttctgtg 60
gctgctgctc atagcagctg ccttcagccc caggggctc nctgggccag gtaagccccc 120
caactcctta caggaaaggt aaggtaacca cctccagagc tactaggtca gcaagaatct 180
ttacagacnc actgcaaatt c 201

<210> SEQ ID NO 11
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is C or A

```
<400> SEQUENCE: 11
ggtgtgttgt  ccttcctggt  tcagagatgc  aactatgtgc  agggctgctg  agctctctct      60
gcatctgggt  gggagcctaa  tggaagtttt  ggggctcctt  nctggtctcc  aaaatcctca     120
agaccaccat  gtgaacacag  gaatcaagga  aggttcttag  atcgactcat  cccccaggcc     180
tttggtttcc  ttgctccttt  c                                                  201

<210> SEQ ID NO 12
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is G or A

<400> SEQUENCE: 12
ggttaagtaa  gttgtccatg  gtatcacagc  tagtcagtca  cagagccatc  atccaaatgc      60
agatatcctg  aattcaggtt  ctacattaga  ctaacccacc  nggaatggag  caggaaagaa     120
cagggaagac  tccacatttt  tggcctctat  ttggtaatta  tagttaactt  tttaggtaat     180
tatagaccaa  ttatcctaga  t                                                  201

<210> SEQ ID NO 13
<211> LENGTH: 201
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is T or C

<400> SEQUENCE: 13
tcttttctgc  tcttaagatc  agaataatcc  agttcatcct  aaaatgcttt  ttctttgtgg      60
tttattttcc  agatgcaatc  aatgccccag  tcacctgctg  ntataacttc  accaatagga     120
agatctcagt  gcagaggctc  gcgagctata  gaagaatcac  cagcagcaag  tgtcccaaag     180
aagctgtgat  gtgagttcag  c                                                  201
```

GENETIC ANALYSES PREDICTIVE OF ASTHMA

CROSS REFERENCE TO RELATED APPLICATIONS

The present application is U.S. national stage of international application PCT/US2008/000524, which had an international filing date of Jan. 16, 2008, and which was published in English under PCT Article 21(2) on Jul. 24, 2008. The benefit of U.S. provisional application 60/880,709, filed on Jan. 17, 2007, is claimed and the contents of this prior application is hereby incorporated by reference in its entirety.

STATEMENT OF GOVERNMENT FUNDING

The United States Government has a paid-up license in this invention and the right in limited circumstances to require the patent owner to license others under reasonable terms as provided for by the terms of NIH Grant No. HL067664, awarded by the Department of Health and Human Services.

FIELD OF THE INVENTION

The present invention is directed to genetic assays for predicting if a subject will develop asthma. Individuals with a combination of certain polymorphic forms of the CCL11 gene, the CCL2 gene and TLR7 gene have a high likelihood of becoming asthmatic.

BACKGROUND OF THE INVENTION

Asthma is a complex disease affecting an estimated 20.5 million Americans and costing the US approximately $16.1 billion annually in health care expenses.[1] Models for predicting adult asthma proposed to date have been constructed using clinical characteristics. Measures that have been found to be significant independent predictors include lung function, airway hyperresponsiveness, atopy, parental history of asthma, and female gender.[5, 6] Although a parental history has been found to be a predictor of asthma, genetic data have not been used to investigate this phenomenon.[5]

Asthma results from the complex interaction of multiple genetic and environmental factors, which causes its phenotypic expression to vary across individuals. In genetic association studies, over 100 genes have been associated with asthma- and atopy-related phenotypes.[7] Of these genes, 25 have been associated in six or more populations and 54 have been associated in two to five populations. None of the single-gene association studies to date has developed a reliable predictive model of asthma. Because asthma is a prototypical complex disease, traditional association studies, which attempt to find single gene associations or assume an additive model of gene interaction are inherently limited in finding complex genetic interactions that may be predictive of asthma.

SUMMARY OF THE INVENTION

The present invention is based upon a novel multivariate method of analysis called Bayesian networks, which are multivariate models able to account for simultaneous associations and interactions among genes to predict asthma status of subjects based on their genotype. Bayesian networks have been successfully used to study gene expression data,[8] protein-protein interactions,[9] and pedigree analysis.[10] They also have been used to model the multigenic association and predict the occurrence of stroke in sickle cell anemia patients, demonstrating the suitability of such networks for understanding the genetic basis of complex diseases and predicting a clinical phenotype.[11] Notwithstanding its recent introduction, the Bayesian network approach is already regarded as an emerging paradigm for the analysis of complex traits.[12,13] Using this approach SNPs were identified that are, in combination, present in patients that are highly susceptible to the development of asthma.

In its first aspect, the invention is directed to a method for diagnostically assessing if a subject is at high risk of developing asthma by determining the polymorphic forms of at least three genes: i) the TLR7 gene (see FIG. 1, SEQ ID NO:1); ii) the CCL11 gene (see FIG. 3, SEQ ID NO:3); and iii) the CCL2 gene (see FIG. 5, SEQ ID NO:5). The term "is at high risk" means that the subject is among a group of people where more than 80% will develop asthma. Among the specific single nucleotide polymorphisms that have been, in combination, found to be characteristic of this group are the ones shown in FIG. 7. These include: rs179019 (SEQ ID NO:7); rs179020 (SEQ ID NO:8); rs179017 (SEQ ID NO:9); rs1129844 (SEQ ID NO:10); rs17735961 (SEQ ID NO:11); rs4795895 (SEQ ID NO:12); and rs4586 (SEQ ID NO:13).

The determination of gene sequences may be carried out using any method known in the art. For example, regions of the TLR7, CCL11 and CCL2 genes may be amplified using the polymerase chain reaction and then sequenced. Alternatively, a DNA microarray may be used in which oligonucleotides that hybridize to specific polymeric forms of genes under conditions of high stringency (e.g., 0.1-0.5×SSC, 50° C.-68° C.) are immobilized on a glass, plastic or nylon support. In general, the oligonucleotides should be 20-500 nucleotides in length and should have sequences that hybridize with TLR7, CCL11 and CCL2. For example, the microarray may include: a) at least one oligonucleotide with a sequence that matches exactly a corresponding sequence in SEQ ID NO:1 except that one nucleotide is replaced with a different nucleotide, a nucleotide is deleted or a nucleotide is added; b) at least one oligonucleotide with a sequence that matches exactly a corresponding sequence in SEQ ID NO:3 but in which one nucleotide is replaced with a different nucleotide, a nucleotide is deleted or a nucleotide is added; and c) at least one oligonucleotide has a sequence that matches exactly a corresponding sequence in SEQ ID NO:5 but in which one nucleotide is replaced with a different nucleotide, a nucleotide is deleted or a nucleotide is added.

In a preferred embodiment the microarray has oligonucleotides that are 20-250 nucleotides in length and there is at least one oligonucleotide that a) has a sequence exactly matching a corresponding sequence in SEQ ID NO:7 and includes the single nucleotide polymorphism of rs179019; b) has a sequence exactly matching a corresponding sequence in SEQ ID NO:8 and includes the single nucleotide polymorphism of rs179017; or c) has a sequence exactly matching a corresponding sequence in SEQ ID NO:9 and includes the single nucleotide polymorphism of rs179017. The microarray may also include at least one oligonucleotide that: a) has a sequence exactly matching a corresponding sequence in SEQ ID NO:10 and includes the single nucleotide polymorphism of rs112944; b) has a sequence exactly matching a corresponding sequence in SEQ ID NO:11 and includes the single nucleotide polymorphism of rs17735961; or c) has a sequence exactly matching a corresponding sequence in SEQ ID NO:12 and includes the single nucleotide polymorphism of rs4795895. In addition, microarrays may include an oligonucleotide exactly matching a corresponding sequence in SEQ ID NO:13 and which includes the single nucleotide polymorphism of rs4586.

The invention also encompasses kits for amplifying nucleic acids using the polymerase chain reaction (PCR) in which there are pairs of primers for amplifying regions of the TLR7, CCL11 and CCL2 genes. These primer pairs may be designed to specifically amplify regions that can be used to determine if the SNPs shown in FIG. 7 are present. Thus, for detecting the form of the TLR7 gene present, a kit may include: a) an oligonucleotide primer pair where one primer has a sequence exactly matching a sequence in SEQ ID NO:7 and which lies at least partially 5' to the single nucleotide polymorphism of rs179019 and a second that has a sequence exactly matching a sequence in SEQ ID NO:7 and which lies at least partially 3' to the single nucleotide polymorphism of rs179019; b) an oligonucleotide primer pair where one primer has a sequence exactly matching a sequence in SEQ ID NO:8 and which lies at least partially 5' to the single nucleotide polymorphism of rs179020 and a second primer with a sequence exactly matching a sequence in SEQ ID NO:8 and which lies at least partially 3' to the single nucleotide polymorphism of rs179020; and/or c) an oligonucleotide primer pair where one primer has a sequence exactly matching a sequence in SEQ ID NO:9 and which lies at least partially 5' to the single nucleotide polymorphism of rs179017 and a second primer that has a sequence exactly matching a sequence in SEQ ID NO:9 and which lies at least partially 3' to the single nucleotide polymorphism of rs179017.

The kit may also include primer pairs for detecting the polymorphic form of the CCL11 gene such as: a) an oligonucleotide primer pair where one primer has a sequence exactly matching a sequence in SEQ ID NO:10 and which lies at least partially 5' to the single nucleotide polymorphism of rs1129844 and a second primer has a sequence exactly matching a sequence in SEQ ID NO:10 and which lies at least partially 3' to the single nucleotide polymorphism of rs1129844; b) an oligonucleotide primer pair where one primer has a sequence exactly matching a sequence in SEQ ID NO:11 and which lies at least partially 5' to the single nucleotide polymorphism of rs17735961 and a second primer that has a sequence exactly matching a sequence in SEQ ID NO:11 and which lies at least partially 3' to the single nucleotide polymorphism of rs17735961; and/or c) an oligonucleotide primer pair where one primer has a sequence exactly matching a sequence in SEQ ID NO:12 and which lies at least partially 5' to the single nucleotide polymorphism of rs4795895 and a second primer has a sequence exactly matching a sequence in SEQ ID NO:12 and which lies at least partially 3' to the single nucleotide polymorphism of rs4795895. The kit can also include primers that amplify regions of the CCL2 gene which may have polymorphisms. For example, it may have a pair of primers where one has a sequence exactly matching a sequence in SEQ ID NO:13 and which lies at least partially 5' to the single nucleotide polymorphism of rs4586 and a second has a sequence exactly matching a sequence in SEQ ID NO:13 and which lies at least partially 3' to the single nucleotide polymorphism of rs4586. In all cases, the primers should be at least 14 nucleotides in length and, in general not longer than about 100 or 200 nucleotides in total.

An association between nucleic acid sequences and the likelihood of developing asthma may also be made at the protein level. Thus, a determination may be made as to whether a subject is at high risk of developing asthma based upon the amino acid sequence of at least: i) the TLR7 gene product (SEQ ID NO:2); ii) the CCL11 gene product (SEQ ID NO:4); and iii) the CCL2 gene product (SEQ ID NO:6). Analysis may be carried out using any method known in the art but immunoassays utilizing antibodies capable of detecting different forms of proteins are generally preferred. The assays may take the form of ELISAs, radioimmunoassay or arrays in which antibodies or proteins are immobilized on a plate, or slide. Techniques such as SELDI-MS (surface enhanced laser desorption/ionization mass spectrometry) may also prove useful.

BRIEF DESCRIPTION OF THE DRAWINGS

FIG. 1: Human TLR7 Reference Nucleotide Sequence. The sequence shown in the figure is designated herein as SEQ ID NO: 1.

FIG. 2: Human TLR7 Gene Product. The amino acid sequence shown in the figure is designated herein as SEQ ID NO:2.

FIG. 3: Human CCL11 Reference Nucleotide Sequence. The sequence shown in the figure is designated herein as SEQ ID NO:3.

FIG. 4: Human CCL11 Gene Product. The amino acid sequence shown in the figure is designated herein as SEQ ID NO:4.

FIG. 5: Human CCL2 Reference Nucleotide Sequence. The sequence shown in the figure is designated herein as SEQ ID NO:5.

FIG. 6: Human CCL2 Gene Product. The amino acid sequence shown in the figure is designated herein as SEQ ID NO:6.

FIG. 7: Seven SNPs Characteristic of Asthma: The sequences shown in the figure have the following sequence identifiers:

| TLR7: | rs179019: | SEQ ID NO: 7 |
|---|---|---|
| | rs179020: | SEQ ID NO: 8 |
| | rs179017: | SEQ ID NO: 9 |
| CCL11: | rs1129844: | SEQ ID NO: 10 |
| | rs17735961: | SEQ ID NO: 11 |
| | rs4795895: | SEQ ID NO: 12 |
| CCL2 | rs4586 | SEQ ID NO: 13 |

DESCRIPTION OF THE INVENTION

The present invention is based upon an association between sequence variations occurring in a combination of three genes and the subsequent development of asthma. In particular, the genes are the human TLR7 gene (Gene ID 51284, see NCBI sequence NM_016562 and NP_057646, see also, Morris, et al., *FASEB J* 20(12):2153-2155 (2006)); the human CCL11 gene (Gene ID 6356, see NCBI sequence NM_002986 and NP_002977, see also, Mir, et al., *Parasite Immunol.* 28:397-400 (2006)); and CCL2 (see NCBI sequence NM_002982 and NP_002973, see also, Lee, et al., *J. Gen. Virol.* 87(pt12):3623-3630 (2006)).

Methods for genotyping individuals to determine the forms of TLR7, CCL11 and CCL2 present are well established in the art. Typically these methods involve a step in which relevant sequences are amplified by PCR. The "Examples" section below provides guidance concerning appropriate procedures but it will be recognized by those of skill in the art that alternatives can also be used. All of the gene sequences required for selecting primers are known and reagents for performing amplifications are commercially available.

Microarrays may also be used in looking for new SNPs and in detecting those that have already been associated with the development of asthma. New SNPs may be looked for by immobilizing sequences that match the known sequences for TLR7, CCL11 and CCL2 but in which a single nucleotide is altered. Hybridizations carried out under conditions of high stringency (low salt, e.g., 0.1-0.5×SSC, and high temperature, e.g., 50° C.-68° C.) may then be used to determine whether a corresponding sequence exists in a sample. Correlations between different polymorphisms and the subsequent development of asthma may then be arrived at using the methodology described herein. Plates with oligonucleotides hybridizing to one or more (preferably all) of the seven SNPs described as being associated with asthma herein may also be used and will be of particular value. Samples that indicate that the TLR7, CCL11 and CCL2 genes all have one of the SNPs are an indication that the subject from which they are derived is at very high risk for developing asthma.

The findings presented herein suggest that other alterations in TLR7, CCL11 and CCL2, i.e., beyond the seven SNPs shown in FIG. 7 may also lead to an increased risk of developing asthma. As discussed above, these changes may be determined using analyses of nucleic acids. However, an examination of the proteins made by these genes, both in terms of amino acid sequence and the amount of protein produced, may also be useful.

The identification of individuals likely to develop asthma may lead to earlier diagnosis, earlier treatment and to counseling regarding life style. In addition, the identification of specific genes that together lead to asthma may suggest new areas for research into the causes and treatment of this disease.

EXAMPLES

The present example describes the construction of a Bayesian network using genotypic data from cases with asthma and non-asthmatic controls from the Nurses' Health Study (NHS), one of the largest prospective studies of risk factors for major chronic diseases in women,[14] that effectively predicts asthma status in subjects from two independent populations.

I. Methods

Training Study

DNA was obtained from incident cases of adult asthma (n=428) and non-asthmatic controls (n=422) from the NHS. Cases were white female lifelong nonsmoking adults with a new self-reported physician diagnosis of asthma, and age-matched controls were white female lifelong nonsmoking adults who did not have a self-reported physician diagnosis of asthma or other pulmonary disease. Self-reported health outcomes in the NHS, including asthma, have been found to be reliable indicators of true disease[15].

Independent Study 1

DNA samples from 21 white asthmatic individuals (16 male, 5 female) were obtained from the Environmental Medicine Genome Bank (EMGB), a repository consisting of army recruits from across the country undergoing basic training.[18] DNA samples from 44 apparently healthy and unrelated self-reported European American (n=21; 10 male, 11 female) and African American (n=23; 11 male, 12 female) adults were obtained from the Coriell Institute for Medical Research (Camden, N.J.).

Independent Study 2

DNA samples were obtained from 168 unrelated adults originally recruited for an asthma medication trial in the United States. Subjects were 80 male and 88 female white non-smoking asthmatic patients, who were diagnosed according to American Thoracic Society criteria.[16] Asthma diagnosis was confirmed by reversible airway obstruction (of at least 15 percent) by beta-agonists or methacholine challenge testing. The percent predicted FEV1 values of all patients were 40 to 85 percent of normal after at least eight hours without inhaling beta-agonists. Further details about this population have been published previously.[17] An independent cohort of 69 controls was collected from the NHS solely for the predictive validation of the model built from the training study. These controls were white female lifelong nonsmoking adults who did not have a self-reported physician diagnosis of asthma or other pulmonary disease.

Informed consent was obtained from all participants. The study was approved by the Institutional Review Board of the Brigham and Women's Hospital.

Genotyping

Sixty-six candidate genes were identified as likely to be involved in asthma susceptibility by the Innate Immunity in Heart, Lung, and Blood Disease Programs for Genomic Applications (IIPGA).[19] Single nucleotide polymorphism (SNP) selection was performed such that a small set of tagging SNPs distinguished the common haplotypes of the genes of interest. Haplotypes were inferred using the Bayesian method implemented in PHASE,[20] and SNPs that distinguished the most common haplotypes were identified using the BEST algorithm.[21] Rare SNPs (minor allele frequency less than five percent) were considered for genotyping if the SNP led to a nonconservative amino acid change, implying potential functional significance. Genotyping of the haplotype tagging SNPs (htSNPs) and the nonsynonymous SNPs was performed in the NHS subjects using either multiplexed single-base extension with a Sequenom Mass Spectrometry MALDI-TOF system (SEQUENOM, San Diego, Calif.) or Taqman real-time PCR with an ABI Prism 7900 machine (Applied Biosystems, Foster City, Calif.). Approximately 10 percent of samples were genotyped twice as part of standard quality control procedures.

The seven SNPs that were associated with asthma status in our predictive model were then genotyped using either of the above techniques (Sequenom or Taqman) in the EMGB, Coriell, Sepracor, and independent NHS control subjects to provide independent model validation.

Predictive Model Construction

Following the method proposed by Sebastiani et al.,[11] a Bayesian network was constructed from a set of 850 subjects (428 cases, 422 controls) genotyped at 226 SNPs in 66 genes using Bayesware Discoverer (bayesware.com), a computer program that implements a common Bayesian approach to identify the most probable network of dependency from a dataset.[22] To find such a network, the program explores a space of different network models, scores each model by its posterior probability given the data, and returns the model with maximum posterior probability.

Predictive Validation

The predictive validation of the model built with the training study was assessed by predicting asthma status in each subject of the two independent studies and comparing the predicted risk of asthma to the actual diagnosis of the subject. The probability of asthma given the genotype of an individual subject was calculated using the clique algorithm implemented in Bayesware Discoverer as described previously.[11] The performance of the predictive model was evaluated by calculating receiver operator characteristic (ROC) curves. Convex hulls were estimated for each ROC curve using the Qhull algorithm[23] as implemented in Matlab (Mathworks, Natick, Mass.). The area under the ROC curve convex hull (AURC) was obtained using the trapezoidal rule.[24] The predictive accuracy of the network derived from the original 850 NHS subjects was tested with two independent study populations: (1) EMGB asthma cases (n=21) and Coriell controls (n=44), and (2) Sepracor asthma cases (n=168) and NHS controls (n=69).

II. Results

A Bayesian network was created from SNPs from 66 genes genotyped in 850 NHS subjects (428 asthma cases, 422 controls). The network found that seven SNPs in the TLR7, CCL11, and CCL2 genes modulate the risk of asthma. Of these SNPs, four have a direct effect on asthma status (CCL11_005208/rs3744508, TLR7_007154/rs179019, CCL11_004654/rs17735961, and TLR7_007042/rs179020), and three are indirectly associated through the others (CCL11_003760/rs4795895, CCL2_005972/rs4586, and TLR7_010982/rs179017). CCL11 and TLR7 are the two genes that are directly related to asthma status. CCL2 is related to asthma status through CCL11. Remaining SNPs that were linked to one another in separate networks mostly correspond to SNPs of the same gene. No TLR7, CCL11, or CCL2 SNPs were linked to SNPs of other genes and one TLR7 SNP was not linked to any other node in the network.

The accuracy of this seven-SNP network was tested by using it to predict asthma status in two independent adult populations. The first group, consisting of 21 cases with asthma and 44 controls, was very well differentiated into cases and controls and had an AURC of 0.95. The second independent population, consisting of 168 cases with asthma and 69 controls, was well differentiated into cases and controls by the network with an AURC of 0.82. Although the initial model was constructed using data from females only, tests on the independent study populations, which included male and female cases and controls and black and white controls, were still effective in differentiating cases from controls.

The fundamental role of epistatic interactions was assessed by comparing the ability of each individual SNP to predict asthma to that of using all SNPs. Our results show that these SNPs individually fail to accurately predict asthma status, as demonstrated by the corresponding AURC values of 0.5, the predictive accuracy achieved by random chance. The two SNPs that are nearest the asthma status node in the network have a slightly increased accuracy, but this accuracy is far lower than that resulting from using data of all seven SNPs.

III. Discussion

The present example demonstrates that a multivariate SNP model effectively predicts asthma status in subjects from two independent populations. A predictive model was constructed from genotypic data from white female NHS data, which found that seven SNPs from three genes out of 226 SNPs from 66 genes modulate the risk of asthma. The predictive ability of this model was tested on two independent study populations, including both male and female subjects and black and white controls. These results show that our predictive model is accurate in subjects of either gender and is robust to some measure of racial variability.

The CCL11 and TLR7 genes, which are directly related to asthma status in our model, are known to have a role in asthma-related phenotypes. The product of the CCL11 gene, eotaxin, is a C—C chemokine involved in the recruitment of peripheral blood eosinophils into the lung during acute allergic inflammation,[25] has been found at high levels in bronchoalveolar lavage fluid of asthmatic individuals,[26] and is correlated with asthma severity[27] and airway hyperresponsiveness.[28] TLR7 is a toll-like receptor (TLR) that specifically recognizes viral single-stranded RNA.[29] The activation of TLRs leads to the activation of cytokines and other genes that mediate immune responses.[30] Consistent with the involvement of TLR7 in asthma, a study of mice treated with a TLR7 ligand prevented allergen-induced airway hyperresponsiveness and eosinophilia, and led to decreased IgE levels.[31] The Bayesian network suggests a biological mechanism by which both TLR7 and CCL11 mediate asthma. Based on what is known about both genes, one possible hypothesis is that viral infection with rhinoviruses, common single stranded RNA viruses that are frequently associated with asthma exacerbations in adults,[32] may stimulate TLR7 to activate an eosinophilic inflammatory response that is mediated by CCL11.

We are not aware of any published study to date that has reported on the association of TLR7 variants with asthma or a related phenotype. Previous studies have investigated the association of individual CCL11 variants with asthma and found discrepant results. A recent family-based study found that one CCL11 SNP is associated with asthma among black subjects, and other CLL11 variants are associated with IgE levels among black and white subjects.[33] However, five case-control studies have found no association between CCL11 variants and asthma,[34-38] although some of these studies did find an association with related phenotypes.[36,38] The inconsistency among the results of these single-SNP association studies may be due to the inadequacy of traditional analytic measures to find associations when a gene variant has a biological effect in the context of other genes. Multivariate methods able to account for the interactions underpinning complex biological processes, such as the one used in this example, increase the ability to find association of SNPs to a phenotype because effects that are modulated through complex interactions can be found.

ROC curve analysis suggested that, in the first independent population, a predictive model based upon the sequences discussed above is ideally sensitive (100 percent) and highly specific (84 percent) at its most accurate threshold. By comparison, ROC curve analysis for the second independent population, suggested the model is highly sensitive (95/90/87 percent) for thresholds at which the specificity is lower (54/57/60 percent).

REFERENCES

1. American Lung Association. Trends in Asthma Morbidity and Mortality. New York, N.Y.: Epidemiology and Statistics Unit, Research and Program Services, American Lung Association; 2006.
2. Schatz M, Clark S, Camargo C A, Jr. Sex differences in the presentation and course of asthma hospitalizations. Chest 2006; 129(1):50-5.
3. Moorman J E, Mannino D M. Increasing U.S. asthma mortality rates: who is really dying? J Asthma 2001; 38(1): 65-71.
4. Barnes N. Most difficult asthma originates primarily in adult life. Paediatr Respir Rev 2006; 7(2): 141-4.
5. Jenkins M A, Hopper J L, Bowes G, Carlin J B, Flander L B, Giles G G. Factors in childhood as predictors of asthma in adult life. Bmj 1994; 309(6947):90-3.
6. Toelle B G, Xuan W, Peat J K, Marks G B. Childhood factors that predict asthma in young adulthood. Eur Respir J 2004; 23(1):66-70.

7. Ober C, Hoffjan S. Asthma genetics 2006: the long and winding road to gene discovery. Genes Immun 2006; 7(2): 95-100.
8. Friedman N. Inferring cellular networks using probabilistic graphical models. Science 2004; 303(5659):799-805.
9. Jansen R, Yu H, Greenbaum D, et al. A Bayesian networks approach for predicting protein-protein interactions from genomic data. Science 2003; 302(5644):449-53.
10. Lauritzen S, Sheehan N. Graphical Models for Genetic Analysis. Statist Sci 2004; 18:489-514.
11. Sebastiani P, Ramoni M F, Nolan V, Baldwin C T, Steinberg M H. Genetic dissection and prognostic modeling of overt stroke in sickle cell anemia. Nat Genet 2005; 37(4): 435-40.
12. Farrall M, Morris A P. Gearing up for genome-wide gene-association studies. Hum Mol Genet 2005; 14 Spec No. 2:R157-62.
13. Verzilli C J, Stallard N, Whittaker J C. Bayesian graphical models for genomewide association studies. Am J Hum Genet 2006; 79(1):100-12.
14. Colditz G A. The Nurses' Health Study: a cohort of US women followed since 1976. J Am Med Womens Assoc 1995; 50(2):40-4.
15. Camargo C A, Jr., Weiss S T, Zhang S, Willett W C, Speizer F E. Prospective study of body mass index, weight change, and risk of adult-onset asthma in women. Arch Intern Med 1999; 159(21):2582-8.
16. Standards for the diagnosis and care of patients with chronic obstructive pulmonary disease (COPD) and asthma. Am Rev Respir Dis 1987; 136(1):225-44.
17. Baron R M, Palmer L J, Tantisira K, et al. DNA sequence variants in epithelium-specific ETS-2 and ETS-3 are not associated with asthma. Am J Respir Crit Care Med 2002; 166(7):927-32.
18. Sonna L, Zhao L, Angel K, Cullivan M, Lilly C. US Army Research Institute of Environmental Medicine. Environmental Medicine Genome Bank Current Composition. USARIEM Technical Note TN00-8 July, 2000.
19. Lazarus R, Vercelli D, Palmer L J, et al. Single nucleotide polymorphisms in innate immunity genes: abundant variation and potential role in complex human disease. Immunol Rev 2002; 190:9-25.
20. Stephens M, Smith N J, Donnelly P. A new statistical method for haplotype reconstruction from population data. Am J Hum Genet 2001; 68(4):978-89.
21. Sebastiani P, Lazarus R, Weiss S T, Kunkel L M, Kohane I S, Ramoni M F. Minimal haplotype tagging. Proc Natl Acad Sci USA 2003; 100(17):9900-5.
22. Cooper G, F., Herskovits E. A Bayesian Method for the Induction of Probabilistic Networks from Data. Mach Learn 1992; 9(4):309-47.
23. Barber C B, David P D, Hannu H. The quickhull algorithm for convex hulls. ACM Trans Math Softw 1996; 22(4):469-83.
24. Fawcett T. ROC graphs: Notes and Practical Considerations for Researchers (HPL-2003-4): HP Laboratories; 2003.
25. Rothenberg M E. Eotaxin. An essential mediator of eosinophil trafficking into mucosal tissues. Am J Respir Cell Mol Biol 1999; 21(3):291-5.
26. Lamkhioued B, Renzi P M, Abi-Younes S, et al. Increased expression of eotaxin in bronchoalveolar lavage and airways of asthmatics contributes to the chemotaxis of eosinophils to the site of inflammation. J Immunol 1997; 159 (9):4593-601.
27. Lilly C M, Woodruff P G, Camargo C A, Jr., et al. Elevated plasma eotaxin levels in patients with acute asthma. J Allergy Clin Immunol 1999; 104(4 Pt 1):786-90.
28. Ying S, Robinson D S, Meng Q, et al. Enhanced expression of eotaxin and CCR3 mRNA and protein in atopic asthma. Association with airway hyperresponsiveness and predominant co-localization of eotaxin mRNA to bronchial epithelial and endothelial cells. Eur J Immunol 1997; 27(12):3507-16.
29. Diebold S S, Kaisho T, Hemmi H, Akira S, Reis e Sousa C. Innate antiviral responses by means of TLR7-mediated recognition of single-stranded RNA. Science 2004; 303 (5663): 1529-31.
30. Means T K, Golenbock D T, Fenton M J. The biology of Toll-like receptors. Cytokine Growth Factor Rev 2000; 11(3):219-32.
31. Moisan J, Camateros P, Thuraisingam T, et al. TLR7 ligand prevents allergen-induced airway hyperresponsiveness and eosinophilia in allergic asthma by a MYD88-dependent and MK2-independent pathway. Am J Physiol Lung Cell Mol Physiol 2006; 290(5):L987-95.
32. Nicholson K G, Kent J, Ireland D C. Respiratory viruses and exacerbations of asthma in adults. Bmj 1993; 307 (6910):982-6.
33. Raby B A, Van Steen K, Lazarus R, Celedon J C, Silverman E K, Weiss S T. Eotaxin polymorphisms and serum total IgE levels in children with asthma. J Allergy Clin Immunol 2006; 117(2):298-305.
34. Hakonarson H, Bjornsdottir U S, Ostermann E, et al. Allelic frequencies and patterns of single-nucleotide polymorphisms in candidate genes for asthma and atopy in Iceland. Am J Respir Crit Care Med 2001; 164(11):2036-44.
35. Chae S C, Lee Y C, Park Y R, et al. Analysis of the polymorphisms in eotaxin gene family and their association with asthma, IgE, and eosinophil. Biochem Biophys Res Commun 2004; 320(1):131-7.
36. Shin H D, Kim L H, Park B L, et al. Association of Eotaxin gene family with asthma and serum total IgE. Hum Mol Genet 2003; 12(11):1279-85.
37. Miyamasu M, Sekiya T, Ohta K, et al. Variations in the human CC chemokine eotaxin gene. Genes Immun 2001; 2(8):461-3.
38. Nakamura H, Luster A D, Nakamura T, et al. Variant eotaxin: its effects on the asthma phenotype. J Allergy Clin Immunol 2001; 108(6):946-53.
39. Punglia R S, D'Amico A V, Catalona W J, Roehl K A, Kuntz K M. Effect of verification bias on screening for prostate cancer by measurement of prostate-specific antigen. N Engl J Med 2003; 349(4):335-42.
40. Pisano E D, Gatsonis C, Hendrick E, et al. Diagnostic performance of digital versus film mammography for breast-cancer screening. N Engl J Med 2005; 353(17): 1773-83.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of assessing if a subject is at high risk of developing asthma, comprising:
   a) analyzing nucleic acid derived from said subject by performing a biological assay to determine whether the following polymorphic forms of the TLR7, CCL11, and CCL2 genes of said subject are present:
      i) a TLR7 gene (SEQ ID NO:1) comprising the single nucleotide polymorphism of rs179019 (SEQ ID NO:7); rs179020 (SEQ ID NO:8); or rs179017 (SEQ ID NO:9);
      ii) a CCL11 gene (SEQ ID NO:3) comprising the single nucleotide polymorphism of rs1129844 (SEQ ID NO:10); rs17735961 (SEQ ID NO:11); or rs4795895 (SEQ ID NO:12); and
      iii) a CCL2 gene (SEQ ID NO:5) comprising the single nucleotide polymorphism of: rs4586 (SEQ ID NO:13);
   b) correlating the frequency of combinations of said polymorphic forms with the likelihood said subject is at high risk of developing asthma wherein combinations comprising rs17735961 (SEQ ID NO: 11), rs 179019 (SEQ ID NO: 7), rs1129844 (SEQ ID NO:10) and rs 179020 (SEQ ID NO: 8) have a direct effect on asthma status and combinations comprising rs4795895 (SEQ ID NO: 12), rs179017 (SEQ ID NO: 9) and rs4586 (SEQ ID NO: 13) have an indirect effect on asthma through association with the other polymorphic forms.

2. The method of claim 1, wherein said TLR7 gene comprises the single nucleotide polymorphism of: rs179019 (SEQ ID NO:7).

3. The method of claim 1, wherein said TLR7 gene comprises the single nucleotide polymorphism of: rs179020 (SEQ ID NO:8).

4. The method of claim 1, wherein said TLR7 gene comprises the single nucleotide polymorphism of: rs179017 (SEQ ID NO:9).

5. The method of claim 1, wherein said CCL11 gene comprises the single nucleotide polymorphism of: rs1129844 (SEQ ID NO:10).

6. The method of claim 1, wherein said CCL11 gene comprises the single nucleotide polymorphism of: rs17735961 (SEQ ID NO:11).

7. The method of claim 1, wherein said CCL11 gene comprises the single nucleotide polymorphism of: rs4795895 (SEQ ID NO:12).

8. The method of claim 1, wherein said polymorphic forms are detected by PCR amplification of nucleic acid derived from said subject followed by sequence analysis of the amplified DNA.

9. The method of claim 1, wherein said method is performed using a DNA microarray, comprising oligonucleotides immobilized on a glass, plastic or nylon support, wherein said oligonucleotides are 20-500 nucleotides in length and wherein:
   a) at least one oligonucleotide has a sequence that matches exactly a corresponding sequence in SEQ ID NO:1 but in which one nucleotide in said corresponding sequence is replaced with a different nucleotide;
   b) at least one oligonucleotide has a sequence that matches exactly a corresponding sequence in SEQ ID NO:3 but in which one nucleotide in said corresponding sequence is replaced with a different nucleotide; and
   c) at least one oligonucleotide has a sequence that matches exactly a corresponding sequence in SEQ ID NO:5 but in which one nucleotide in said corresponding sequence is replaced with a different nucleotide.

10. The method of claim 1, wherein said method is performed using a DNA microarray, comprising oligonucleotides that are immobilized on a glass, plastic or nylon support, wherein said oligonucleotides are 20-250 nucleotides in length and wherein at least one oligonucleotide:
    a) has a sequence exactly matching a corresponding sequence in SEQ ID NO:7 and includes the single nucleotide polymorphism of rs179019;
    b) has a sequence exactly matching a corresponding sequence in SEQ ID NO:8 and includes the single nucleotide polymorphism of rs179017; or
    c) has a sequence exactly matching a corresponding sequence in SEQ ID NO:9 and includes the single nucleotide polymorphism of rs179017.

11. The method of claim 10, wherein said DNA microarray further comprises at least one oligonucleotide that:
    a) has a sequence exactly matching a corresponding sequence in SEQ ID NO:10 and includes the single nucleotide polymorphism of rs112944;
    b) has a sequence exactly matching a corresponding sequence in SEQ ID NO:11 and includes the single nucleotide polymorphism of rs17735961; or
    c) has a sequence exactly matching a corresponding sequence in SEQ ID NO:12 and includes the single nucleotide polymorphism of rs4795895.

12. The method of claim 10, wherein said DNA microarray further comprises an oligonucleotide exactly matching a corresponding sequence in SEQ ID NO:13 and includes the single nucleotide polymorphism of rs4586.

13. The method of claim 1, wherein said method is performed using a kit for amplifying nucleic acids by the polymerase chain reaction (PCR), said kit comprising:
    a) an oligonucleotide primer at least 14 nucleotides in length and that has a sequence exactly matching a sequence in SEQ ID NO:7 and which lies at least partially 5' to the single nucleotide polymorphism of rs179019 and a second oligonucleotide primer at least 14 nucleotides in length and that has a sequence exactly matching a sequence in SEQ ID NO:7 and which lies at least partially 3' to the single nucleotide polymorphism of rs179019;
    b) an oligonucleotide primer at least 14 nucleotides in length and that has a sequence exactly matching a sequence in SEQ ID NO:8 and which lies at least partially 5' to the single nucleotide polymorphism of rs179020 and a second oligonucleotide primer at least 14 nucleotides in length and that has a sequence exactly matching a sequence in SEQ ID NO:8 and which lies at least partially 3' to the single nucleotide polymorphism of rs 179020; and/or
    c) an oligonucleotide primer at least 14 nucleotides in length and that has a sequence exactly matching a sequence in SEQ ID NO:9 and which lies at least partially 5' to the single nucleotide polymorphism of rs179017 and a second oligonucleotide primer at least 14 nucleotides in length and that has a sequence exactly matching a sequence in SEQ ID NO:9 and which lies at least partially 3' to the single nucleotide polymorphism of rs179017.

14. The method of claim 13, wherein said kit further comprises:
    a) an oligonucleotide primer at least 14 nucleotides in length and that has a sequence exactly matching a sequence in SEQ ID NO:10 and which lies at least partially 5' to the single nucleotide polymorphism of rs1129844 and a second oligonucleotide primer at least 14 nucleotides in length and that has a sequence exactly matching a sequence in SEQ ID NO:10 and which lies at least partially 3' to the single nucleotide polymorphism of rs1129844;
    b) an oligonucleotide primer at least 14 nucleotides in length and that has a sequence exactly matching a sequence in SEQ ID NO:11 and which lies at least partially 5' to the single nucleotide polymorphism of rs17735961 and a second oligonucleotide primer at least 14 nucleotides in length and that has a sequence exactly matching a sequence in SEQ ID NO:11 and which lies at least partially 3' to the single nucleotide polymorphism of rs17735961; and/or
    c) an oligonucleotide primer at least 14 nucleotides in length and that has a sequence exactly matching a sequence in SEQ ID NO:12 and which lies at least partially 5' to the single nucleotide polymorphism of rs4795895 and a second oligonucleotide primer at least 14 nucleotides in length and that has a sequence exactly matching a sequence in SEQ ID NO:12 and which lies at least partially 3' to the single nucleotide polymorphism of rs4795895.

15. The method of claim 13 wherein said kit further comprises an oligonucleotide primer at least 14 nucleotides in length and that has a sequence exactly matching a sequence in SEQ ID NO:13 and which lies at least partially 5' to the single nucleotide polymorphism of rs4586 and a second oligonucleotide primer at least 14 nucleotides in length and that has a sequence exactly matching a sequence in SEQ ID NO:13 and which lies at least partially 3' to the single nucleotide polymorphism of rs4586.

16. The method of claim 2, wherein said CCL11 gene comprises the single nucleotide polymorphism of: rs1129844 (SEQ ID NO:10).

* * * * *